United States Patent
Kaneyama et al.

(10) Patent No.: US 7,498,573 B2
(45) Date of Patent: Mar. 3, 2009

(54) METHOD FOR OBTAINING AND PROCESSING SURFACE ANALYSIS DATA

(75) Inventors: Miyuki Kaneyama, Tokyo (JP); Masumi Katagami, Tokyo (JP)

(73) Assignee: Jeol Ltd., Tokyo (JP)

( * ) Notice: Subject to any disclaimer, the term of this patent is extended or adjusted under 35 U.S.C. 154(b) by 229 days.

(21) Appl. No.: 11/656,888

(22) Filed: Jan. 23, 2007

(65) Prior Publication Data

US 2008/0029698 A1    Feb. 7, 2008

(30) Foreign Application Priority Data

Jan. 23, 2006    (JP)    ............... 2006-014207

(51) Int. Cl.
*G01N 23/223*    (2006.01)

(52) U.S. Cl. ........................ 250/310; 378/45
(58) Field of Classification Search ................ 250/310; 378/45; 702/19
See application file for complete search history.

(56) References Cited

U.S. PATENT DOCUMENTS 4,288,692 A * 9/1981 Schamber et al. ........... 250/310
6,404,847 B1 * 6/2002 Ueki et al. .................... 378/45

FOREIGN PATENT DOCUMENTS

JP    61-093938    5/1986

\* cited by examiner

*Primary Examiner*—Kiet T Nguyen
(74) *Attorney, Agent, or Firm*—The Webb Law Firm (57) ABSTRACT

A method of managing data obtained by measurements. The method permits EDS (energy dispersive spectroscopy) spectra to be collected in one operation. Energies detected by an EDS detector are converted by a pulse height analyzer into pulses of heights corresponding to the energies. The heights of the pulses in a distribution are assigned to multiple channels. The number of pulses in each channel is counted. A data processing circuit sends data blocks to a CPU. In each data block, a tag indicative of being X-ray energy data and the value of energy are combined. The CPU sequentially stores incoming data blocks into a hard disk.

15 Claims, 4 Drawing Sheets

DATA STRUCTURE

FIG.1

FIG.2A DATA STRUCTURE

METHOD FOR OBTAINING AND PROCESSING SURFACE ANALYSIS DATA

BACKGROUND OF THE INVENTION

1. Field of the Invention

The present invention relates to a method of obtaining and processing (managing) data obtained by a measurement or measurements (hereinafter referred to as "measurement data") using a surface analysis instrument, such as an electron probe microanalyzer (EPMA), to which an energy dispersive X-ray spectrometer (EDS) is attached. The invention also relates to a measurement data structure adapted for this method. Furthermore, the invention relates to a method of reproducing a spectrum from measurement data having the above-described measurement data structure and to a surface analysis instrument using the measurement data structure.

2. Description of Related Art

Heretofore, a technique for detecting chemical elements present in a desired region on the surface of a sample using an energy dispersive X-ray spectrometer (EDS) has been known as disclosed in Japanese Patent Laid-Open No. S61-93938. In particular, the desired region is scanned in two dimensions with an electron beam by moving the beam relative to the sample. As the sample is scanned, X-rays are produced from the sample. The produced X-rays are spectrally analyzed by the EDS, and the number of photons present in each energy range is counted. Information about the obtained counts is processed to identify the elements present in the region.

The sample that undergoes X-ray spectral analysis using the EDS may be irradiated with a focused ion beam (FIB).

In energy dispersive X-ray spectroscopy (EDS), when the sample is being irradiated with an electron beam, the composition of the sample may vary with the elapse of time. That is, the electron beam irradiation itself may vary the composition. Furthermore, where the sample is heated or cooled, the composition may vary according to the heating time or cooling time. In addition, ion beam irradiation may vary the composition.

For example, where the sample is irradiated with an electron beam for 100 seconds, if it is to be examined how the concentration of a certain element contained in the sample varies, the concentration of a certain element in the sample is measured every 10 seconds, and the resulting data is stored. When the variation of the composition is examined every 10 seconds, the sample is irradiated with the electron beam for 10 seconds, and a spectrum is derived and stored. The sample is again irradiated with the beam for 10 seconds, and another spectrum is taken and stored. These process steps are carried out repeatedly. Since the operations for storing spectra are added, it cannot be said that the variation of the composition is examined on a real-time basis.

Where normal data is derived up to an intermediate point in a measurement, if the data is nullified during the measurement by contamination of the sample, the measurement must be redone from the beginning.

Where 10 measurements are performed every 10 seconds in this way, when the resulting file is being saved, the sample is being irradiated with the electron beam in practice. It has not been possible to measure the correct variation occurring during the irradiation of 100 seconds.

If the human analyzer recognizes that the time resolution of 10 seconds is too low, a new measurement must be performed at a different location provided that there is sample damage. That is, where the composition was attempted to be investigated every 10 seconds and then the human analyzer wants to perform measurements at a higher time resolution of 5 seconds rather than 10 seconds, the composition has varied during the process. Therefore, it is impossible to perform the same measurement at the same location. In this way, it has been impossible to derive data that would be identical with data obtained from 5 second-interval measurements after measurements were performed at intervals of 10 seconds in practice.

Furthermore, where a sample is irradiated with a focused ion beam for 100 seconds, there has been no means for investigating the relationship between the variation in the intensity of a certain chemical element contained in the sample and the process of creating the sample using the focused ion beam if it is desirable to utilize such means.

Any of the above-described conventional works has been cumbersome and laborious to perform.

SUMMARY OF THE INVENTION

It is an object of the present invention to provide a method of managing measurement data in such a way that all EDS spectra, for example, can be obtained in one measurement. It is another object of the present invention to provide a measurement data structure adapted for this method. It is a further object of the present invention to provide a surface analysis instrument implementing this method. It is yet another object of the present invention to provide a method of reproducing a spectrum using such measurement data.

Furthermore, it is an object of the present invention to provide a method of managing measurement data in such a way that spectra occurring at desired intervals of time can be obtained in association with a process of creating a sample after performing only one measurement for deriving EDS spectra It is another object of the present invention to provide a measurement data structure adapted for this method. It is a further object of the present invention to provide a surface analysis instrument adapted to implement this method.

A method of obtaining and processing (managing) measurement data in accordance with one embodiment of the present invention is implemented by a surface analysis instrument. The method starts with detecting secondary rays produced by exciting a sample. The energies of the detected secondary energies are analyzed. Energy data blocks including (i) tags indicative of being data about the analyzed energies and (ii) data about the energies are created. Elapsed time data blocks including (i) tags indicative of being data about elapsed times of measurement and (ii) data about the elapsed times are created. This process step may be hereinafter referred to as the data processing step. The created energy data blocks and elapsed time data blocks are recorded in a recording medium. This process step may be hereinafter referred to as the control step. Preferably, during the data processing step, effective elapsed time data blocks are created. The effective elapsed time data blocks include (i) tags indicative of being data about effective elapsed times and (ii) data about the effective elapsed times. Preferably, during the data processing step, energy data blocks and elapsed time data blocks are created whenever secondary rays are entered. Preferably, during the control step, the energy data blocks whose numbers are variable are arranged between adjacent ones of the elapsed time data blocks according to the secondary rays.

A data structure associated with one embodiment of the present invention is associated with data obtained by measurements using a surface analysis instrument. Secondary rays produced by exciting a sample are detected. The energies of the detected secondary rays are analyzed. Energy data blocks including (i) tags indicative of being data about the analyzed energies and (ii) data indicative of the energies are created. Furthermore, elapsed time data blocks including (i) tags indicative of being data about elapsed times of measurement and (ii) data about the elapsed times are created. The energy data blocks whose numbers are variable are placed between adjacent ones of the elapsed time data blocks according to the secondary rays.

A method of reproducing a spectrum in accordance with one embodiment of the present invention is implemented to reproduce a spectrum from data obtained by measuring secondary rays using a surface analysis instrument. The method starts with exciting a sample and detecting resulting secondary rays. The energies of the detected secondary rays are analyzed. Energy data blocks including (i) tags indicative of being data about the analyzed energies and (ii) data about the energies are created. Elapsed time data blocks including (i) tags indicative of being data about elapsed times of measurement and (ii) data about the elapsed times are created. This process step may be hereinafter referred to as the data processing step. The created energy data blocks and elapsed time data blocks are recorded in a storage medium. This process step may be hereinafter referred to as the control step. The energy data blocks are reproduced and displayed according to the elapsed time data blocks recorded in the storage medium as described previously. In the data processing step, energy data blocks and elapsed time data blocks are preferably created whenever secondary rays are entered. In the control step, the energy data blocks whose numbers are variable are preferably placed between adjacent ones of the elapsed time data blocks according to the secondary rays.

A method of obtaining and processing (managing) measurement data in accordance with one embodiment of the present invention is implemented to manage data obtained by measurements using a surface analysis instrument. The method starts with exciting a sample to produce secondary rays. The secondary rays are detected. The energies of the detected secondary rays are analyzed. Energy data blocks including (i) tags indicative of being data about the analyzed energies and (ii) data about the energies are created. Data about elapsed times of measurement are added to the energy data blocks. This process step may be hereinafter referred to as the data processing step. Energy data blocks created by the data processing step are recorded in a storage medium. Preferably, in the data processing step, information about two-dimensional positions is also stored in the energy data blocks.

A data structure associated with one embodiment of the present invention is associated with data obtained by measurements using a surface analysis instrument. A sample is excited to produce secondary rays. The secondary rays are detected. The energies of the detected secondary rays are analyzed. Energy data blocks including (i) tags indicative of being data about the analyzed energies and (ii) data about the energies are created. Data about elapsed times of measurement are added to the energy data blocks. The energy data blocks created in this way are arranged. Preferably, information about two-dimensional positions is also stored in the energy data blocks.

A method of obtaining and processing (managing) measurement data in accordance with one embodiment of the present invention is implemented to manage data obtained by measurements using a surface analysis instrument. The method starts with exciting a sample to produce secondary rays. The secondary rays are detected. The energies of the detected secondary rays are analyzed. Energy data blocks including (i) tags indicative of being data about the analyzed energies and (ii) data about the energies are created. Data about elapsed times of measurement are added to the energy data blocks. This process step may be hereinafter referred to as the data processing step. The created energy data blocks are controlled and recorded in a storage medium. The energy data blocks recorded in the storage medium are reproduced and displayed along the elapsed times. Preferably, in the data processing step, information about two-dimensional positions is also stored within the energy data blocks.

A surface analysis instrument associated with one embodiment of the present invention is used to analyze a surface of a sample. The surface analysis instrument has a beam source for producing a particle beam to be directed at the sample, detection means for exciting the sample with the particle beam supplied from the beam source and detecting produced secondary rays, analysis means for analyzing the energies of secondary rays detected by the detection means, data processing means, and control means. The data processing means creates energy data blocks and elapsed time data blocks. The energy data blocks include (i) tags indicative of being data about the analyzed energies and (ii) data about the energies. The elapsed time data blocks include (i) tags indicative of being data about elapsed times of measurement and (ii) data about the elapsed times. The control means records the created energy data blocks and the elapsed time data blocks in a storage medium. Preferably, the particle beam is a beam of electrons or focused ions. According to an embodiment of the present invention, spectra corresponding to instants of time at any arbitrary intervals can be obtained only if EDS spectra are measured in one operation.

Furthermore, where data are nullified during measurement due to sample contamination, effective data can be obtained by constructing spectra corresponding to the instants of time prior to the instant when data were nullified.

Spectra corresponding to arbitrary instants of time can be obtained in an associated manner with the process of creating the sample simply by measuring EDS spectra in one operation.

Other objects and features of the invention will appear in the course of the description thereof, which follows.

DESCRIPTION OF THE PREFERRED EMBODIMENTS

The preferred embodiments of the present invention are hereinafter described with reference to the accompanying drawings.

Figure 1:
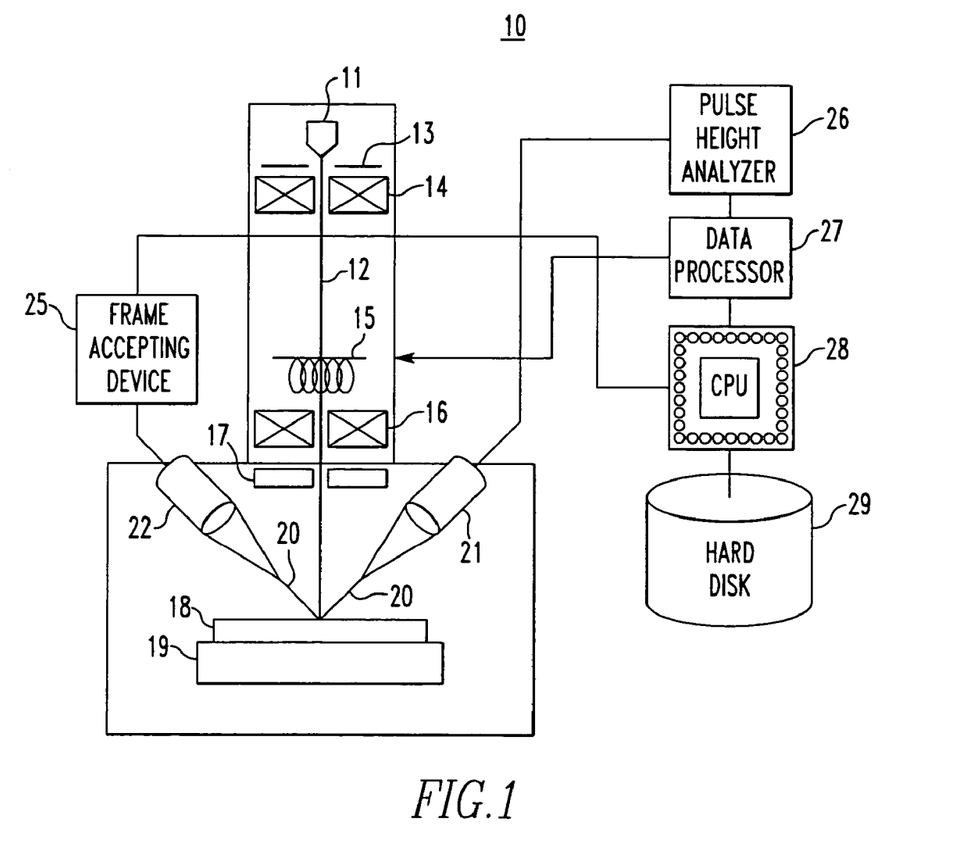
FIG. 1 is a diagram of a surface analysis instrument according to one embodiment of the present invention.

FIG. 1 is a diagram of a surface analysis instrument according to one embodiment of the present invention. The surface analysis instrument consists of an electron probe microanalyzer (EPMA), generally indicated by reference numeral 10. The instrument has an electron gun 11 emitting an electron beam which is directed at a sample to produce secondary rays (X-rays in this embodiment) from the sample. The secondary rays are spectrally analyzed by an energy dispersive X-ray spectrometer (EDS) 21. The obtained spectrum is analyzed, reproduced, and displayed on a display device (not shown) by a pulse height analyzer (PHA) 26 (described later) forming a computer, a data processing circuit 27, and a CPU 28. The display device is connected with the CPU 28. It is assumed that the recorded energies of photons are described as a function of time.

The electron beam 12 emitted from the electron gun 11 is sharply focused by a slit 13, a condenser lens 14, and an objective lens 16 and focused onto a sample 18. An electron beam deflection coil 15 is mounted ahead of the objective lens 16 to permit the user to select any desired beam position on the sample 18 or to enable two-dimensional scanning of the beam 12 over the surface of the sample. The deflection coil 15 is under control of the data processing circuit 27. X-rays 20 emitted from the sample 18 by the irradiation by the beam 12 enter the EDS detector 21. The output signal from the detector 21 is sent to the data processing circuit 27 through the pulse height analyzer 26.

The sample 18 is placed on a sample stage 19, which is connected with drive motors to drive the stage in the X- and Y-directions perpendicular to the direction of the optical axis of the electron beam 12. The drive motors are connected with stage control circuitry (not shown).

The EDS detector 21 detects variations of energies of the X-rays 20 produced from the sample 18. The X-rays 20 emanating from the sample 18 are also detected by a backscattered electron imaging (BSE) detector 17 and a secondary electron imaging (SEI) detector 22. The image detected by the imaging detector 22 is accepted into a frame accepting device 25 for every frame and sent to the CPU (central processing unit) 28.

The pulse height analyzer 26 converts the energy detected by the EDS detector 21 into a pulse of a height corresponding to the energy, assigns the heights of such pulses in a distribution to multiple channels, and counts the number of pulses in each channel.

The data processing circuit 27 creates data about combinations of tags indicative of being data about the energies of the X-rays 20 and energy values (hereinafter referred to as the data blocks). The created data blocks are sent to the CPU 28. The data processing circuit 27 also operates to control the electron beam deflection coil 15.

The CPU 28 receives the incoming data blocks and stores the blocks in a hard disk 29 in succession.

Apart from the above-described operation, the data processing circuit 27 combines a tag indicative of being data about an elapsed time of measurement with the elapsed time to form a data block. The data block is sent to the CPU 28. Finally, such data blocks are stored in the hard disk 29. An effective elapsed time is processed similarly.

The elapsed time represents actual passage of time. The effective elapsed time represents the time for which the pulse height analyzer 26 could count the X-rays 20. The pulse height analyzer 26 detects events (each event being information indicating reception of one photon) of the X-rays 20, analyzes the pulse heights, and sends the results to the data processing circuit 27. The events detected during analysis of pulse heights are rejected. In particular, if the number of events occurring per unit time increases, the ratio of rejected events to the processed (actually counted) events increases. As a result, if the obtained counts are normalized with the elapsed time and a count rate is found, the count rate will not be correct. Accordingly, the rejected events are converted into a dead time. During this time interval, the timer is stopped. This is taken as an effective elapsed time. That is, if the measured counts are normalized with the effective elapsed time, a correct count rate is obtained.

Figure 2A:
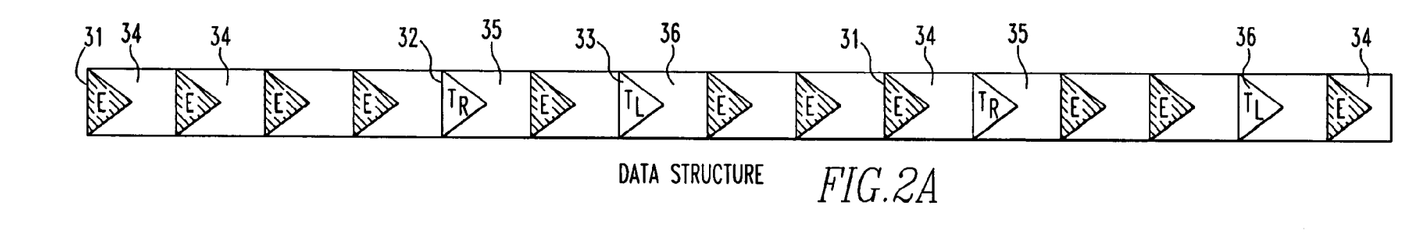
FIG. 2A is a diagram illustrating the structure of data finally recorded in a hard disk under control of a CPU.
Figure 2B:
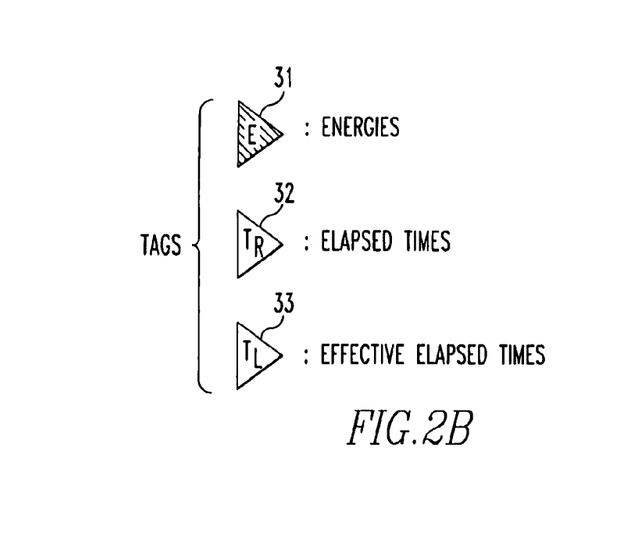
FIG. 2B is a diagram of Tags.
Figure 2C:
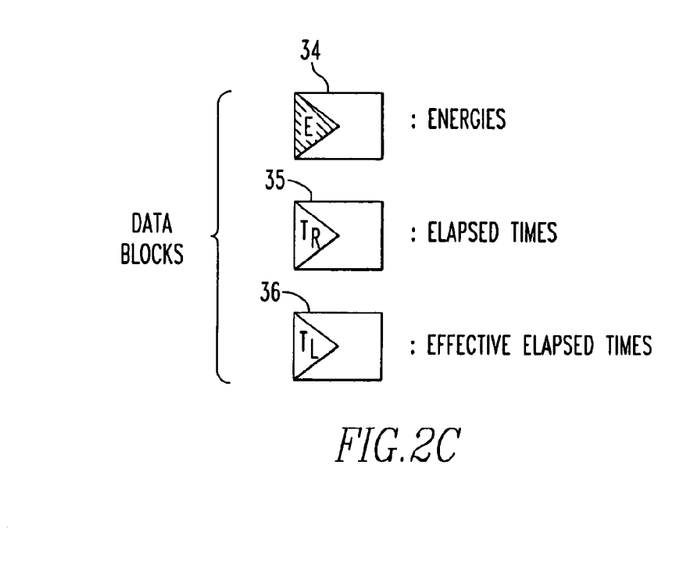
FIG. 2C is a diagram illustrating data blocks.

FIGS. 2A, 2B and 2C illustrate the structure of data finally recorded in the hard disk 29 under control of the CPU 28. This data structure consists of tags 31 indicative of being data about energies, data blocks 34 indicating data about the energies of X-rays, tags 32 indicative of being data about elapsed times, data blocks 35 indicating data about the elapsed times, tags 33 indicative of being data about effective elapsed times, and data blocks 36 indicating data about the effective elapsed times. The CPU 28 places a variable number of energy data blocks between adjacent elapsed time data blocks according to the X-rays.

In FIGS. 2A, 2B and 2C, four (at most) data blocks 34 indicating X-ray energies are placed between the data blocks 35 indicating elapsed times, i.e., between the adjacent data blocks. The data structure is shown to be simplified for simplicity of illustration. In practice, more data blocks 34 can be placed.

The data blocks indicating the energies record channels corresponding to the energies of photons. A spectrum can be reproduced by accumulating these channels with the elapse of time. For example, where channels are recorded by inserting a tag $T_R$ indicative of being data about an elapsed time every 0.1 ms, a histogram is created until the number of appearing tags $T_R$ reaches 10 k, and a spectrum can be reproduced. Consequently, a spectrum can be derived every 1 second. Obviously, the interval between the tags indicative of elapsed times is not limited to 0.1 ms.

In this way, according to the present embodiment, once data are collected, any arbitrary time division can be performed simply by determining how many tags are inserted or how long a time interval is used.

Where the measured energy range and the total number of channels are previously known, if channel numbers are described instead of data about the energies of X-rays, exactly the same results can be obtained. Similarly, the time can be measured by producing a pulse or pulses indicative of the elapsed time at regular intervals of time instead of values of the elapsed time and effective elapsed time and recording a time tag at the timing at which the pulse is produced.

The premise is that the data structure described so far is adopted. Alternatively, a structure created by recording the whole spectrum consisting of fixed-length channels at regular intervals of time may also be adopted.

A procedure for reproducing a spectrum from the data structure shown in FIGS. 2A, 2B and 2C is next described. An example of data structure is discussed in which X-ray energies are counted in channels and a tag of elapsed time is recorded at regular intervals of 0.1 ms.

A spectrum is constructed from the above-described data every 10 seconds with the elapse of time as listed in Table 1 below. Spectra up to 10 seconds correspond to appearance frequencies of energy data in each channel plotted until the 100,000th time tag appears. A period of 10 seconds passes until the 100,000th time tag appears. A period of 20 seconds passes until the 200,000th time tag appears. A period of 30 seconds passes until the 300,000th time tag appears.

TABLE 1

| time tags | spectra |
|---|---|
| from 0 to 100k | spectra from 0 to 10 seconds |
| from 101k to 200k | spectra from 10 to 20 seconds |
| from 201k to 300k | spectra from 20 to 30 seconds |
| from 301k to 400k | spectra from 30 to 40 seconds |

If each counted time tag indicates an elapsed time, a spectrum corresponding to an actually elapsed time is obtained.

On the other hand, if each counted time tag indicates an effective time, the obtained spectrum corresponds to an effective time for which X-rays could be counted, i.e., for which a measurement was performed in practice.

Even where a spectrum is constructed based on the elapsed time, it is possible to know the effective time for the spectrum by counting the tags of effective time appearing so far. Of course, the reverse holds. In this way, if a spectrum is constructed, and if the time resolution is not sufficient (i.e., a spectrum of higher time resolution is required), spectra corresponding to every 5 seconds can be obtained from exactly the same data. That is, after spectral data is created in practice, if one wants to create spectra every 5 seconds because the variation was greater than expected, tags are counted similarly from the same data, and spectra can be created every 5 seconds.

In the embodiment described so far, spectra are created at exactly identical intervals of time. Alternatively, spectra may be created at time intervals each starting at 0 as given in Table 2 below.

TABLE 2

| time tags | spectra |
| --- | --- |
| from 0 to 100k | spectra from 0 to 10 seconds |
| from 0 to 200k | spectra from 0 to 20 seconds |
| from 0 to 300k | spectra from 0 to 30 seconds |
| from 0 to 400k | spectra from 0 to 40 seconds |

Spectra from 0 to 10 seconds correspond to the appearance frequencies of energy data plotted for each channel until 0th to 100,000th time tags appear. Spectra from 0 to 20 seconds correspond to the appearance frequencies of energy data plotted for each channel until 0th to 200,000th time tags appear. Similarly, spectra from 0 to 30 seconds correspond to the appearance frequencies of energy data plotted for each channel until 0th to 300,000th time tags appear. Spectra from 0 to 40 seconds correspond to the appearance frequencies of energy data plotted for each channel until 0th to 400,000th time tags appear.

Furthermore as shown in Table 3, in a case where a sample was irradiated with ions for 30 seconds since a period of 10 seconds passed from the beginning of a measurement of a spectrum, it is also possible to create a fine spectrum every 5 seconds only during the ion irradiation.

TABLE 3

| time tags | | spectra |
| --- | --- | --- |
| from 0 to 100k | | spectra from 0 to 10 seconds |
| from 101k to 150k | ion | spectra from 10 to 15 seconds |
| from 151k to 200k | irradiation | spectra from 15 to 20 seconds |
| from 201k to 250k | | spectra from 20 to 25 seconds |
| from 251k to 300k | | spectra from 25 seconds to 30 seconds |
| from 301k to 350k | | spectra from 30 seconds to 35 seconds |
| from 351k to 400k | | spectra from 35 seconds to 40 seconds |
| from 401k to 500k | | spectra from 40 to 50 seconds |

Ion irradiation is done for a period of 30 seconds from an instant of 10 seconds to an instant of 40 seconds. During this period, spectra occurring at intervals of 5 seconds (e.g., from an instant of 10 seconds to an instant of 15 seconds) can be grasped when from 101,000th to 150,000th time tags appear. Furthermore, spectra from an instant of 15 seconds to an instant of 20 seconds can be grasped when from 151,000th to 200,000th time tags appear. Similarly, spectra from an instant of 20 seconds to an instant of 25 seconds can be grasped when from 201,000th to 250,000th time tags appear. Spectra from an instant of 25 seconds to an instant of 30 seconds can be grasped when from 251,000th to 300,000th time tags appear. Spectra from an instant of 30 seconds to an instant of 35 seconds can be grasped when from 301,000th to 350,000th time tags appear. Spectra from an instant of 35 seconds to an instant of 40 seconds can be grasped when from 351,000th to 400,000th time tags appear. After the end of the 30 second ion irradiation, spectra from an instant of 40 seconds to an instant of 50 seconds can be grasped when from 401,000th to 500,000th time tags appear.

In this way, the electron probe microanalyzer (EPMA) 10 shown in FIG. 1 detects secondary rays (e.g., X-ray photons or electrons) secondarily produced when the sample is excited or secondary rays to which different energy values were imparted by interaction of exciting primary rays with the sample, and records the magnitudes of energies and information about occurrence of events. The microanalyzer 10 displays timewise variations of the secondary rays on the display device (not shown) connected with the CPU 28, based on the recorded information about the time and energy values. For example, the temperature can be varied, and deposition or phase variations can be recorded and displayed.

In the past, measurement and recording have been repeated a preset number of times. Consequently, there has been a danger that if there is a trace amount of component, and if the measurement time is short, the produced spectrum will be buried in the statistically varying baseline. Since the time resolution is determined by the measurement time, if the measurement time is too long, it has been impossible to capture variations in the subject of measurement. Where the results of the measurement are not appropriate, it is necessary to redo the measurement. Because the sample has been already affected by the measurement, it is impossible to reproduce the state.

In contrast, the electron probe microanalyzer 10 requires only simple processing. That is, a measurement time is set and then a measurement is performed by utilizing the measurement data management method, measurement data structure, and spectrum reproduction method according to embodiments of the present invention. Subsequently, conditions under which a display is provided are set and displayed. The measurement time used in the present invention is equal to the total time of repetitive measurements performed by the prior art method. Since each measured value of energy is time stamped, a unit display time is specified for the measured data and the timewise variation can be displayed. After the completion of the measurement, the display conditions may be modified. Consequently, measurement misses can be prevented.

As described so far, in the present embodiment, rays are spectrally analyzed by the EDS detector 21. The obtained spectra are processed by the pulse height analyzer 26 and data processing circuit 27. The data processing circuit 27 is controlled by the CPU 28. The tags indicating the time are added to energy data recorded in the hard disk 29. Because of this data structure, spectra can be easily reproduced and displayed. That is, one embodiment of the present invention is characterized by the method of storing data obtained by measurements. In particular, data are reconstructed using the tags. The method of storing data in accordance with this embodiment of the present invention reduces the amount of data vastly compared with the prior art repetitive method consisting of collecting data for 1 second, storing the data in memory, again collecting data for 1 second, storing the data in memory, and so forth.

In the present embodiment, 2000 channels, for example, can be used as ones corresponding to the energies of events. If an event is detected at intervals of 0.1 ms, for example, as in the present embodiment, the event might be 0. No data is stored in a corresponding manner to such 0 channel. What are stored as a channel in practice are channel numbers from 0 to 2000. This can reduce the amount of data.

Figure 3:
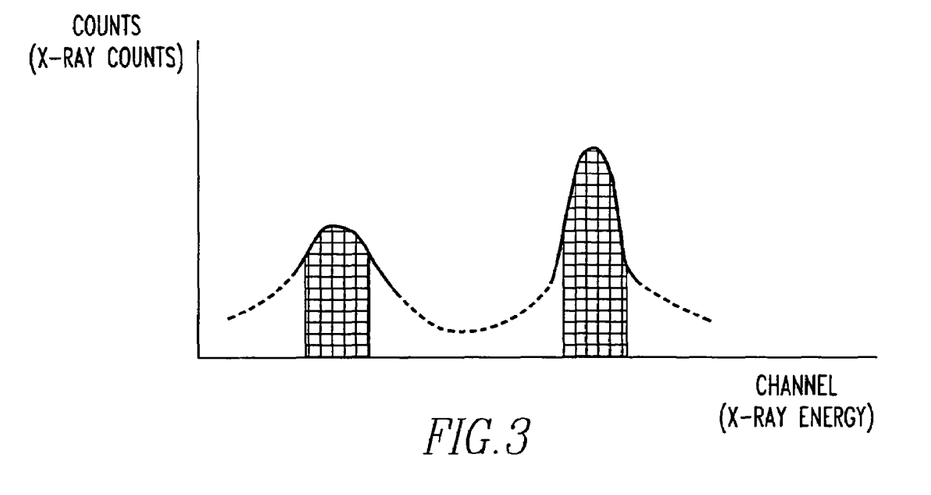
FIG. 3 is a diagram illustrating the manner in which a histogram is created.

FIG. 3 is a schematic view illustrating the manner in which a histogram is created. In order to create the histogram using data as described above, blocks are placed at desired intervals of time on the energy axis indicating channels. For example, if there is channel 1, a block is placed at a location corresponding to this channel 1. If there is channel 10, a block is placed at a location corresponding to this channel 10. The time is detected by detecting time tags. The histogram can be created by sequentially stacking blocks at locations corresponding to channels. This histogram corresponds to spectra in this time. By repeating these operations, spectra can be created at desired intervals of time, e.g., every 10 seconds. A technique for reconstructing spectra at specified intervals of time from EDS spectra measured by the EDS detector has been disclosed so far.

The aforementioned data structure includes data about energies and time tags. It is also possible not to use these tags. That is, a combination (E·τR·τLn) of an energy value (E), an elapsed time (τR), and an effective elapsed time (τLn) is defined as one data block of fixed length.

Information about two-dimensional positions x, y may be stored in such data blocks. Two-dimensional data can also be reproduced by constructing each data block such that plural tags E are sandwiched between tags P indicating coordinates. In this case, the data processing circuit 27 acts as a generator for producing coordinates x, y. During measurement, if photons are detected when a beam is directed at some position, data in which the coordinates x, y are combined with the energies of the photons are created.

Where the data structure does not contain any tag T indicating time in this way, the spectrum can be resolved if the tags P indicating information about the positions (coordinates x, y) are present together with the tags E indicating energies. Of course, tags P, E, T, and other tags (e.g., a tag of temperature) may coexist.

A technique for placing time tags T between tags of energy data has been disclosed. A second technique for placing tags P of information about positions (coordinates) together with tags E of energies has been disclosed.

The technique consisting of reproducing a time-divided spectrum and displaying it leads to a method of storing energy data automatically, for example, every 1 second. That is, if 2000 channels, for example, are collected always every 1 second, spectral data can be recorded.

Furthermore, one embodiment of the present invention makes it possible to reconstruct a spectrum every specified instant of time from an EDS spectrum produced by irradiation of a focused ion beam (FIB). It is also required that the recorded energies of photons be described as a function of time.

Figure 4:
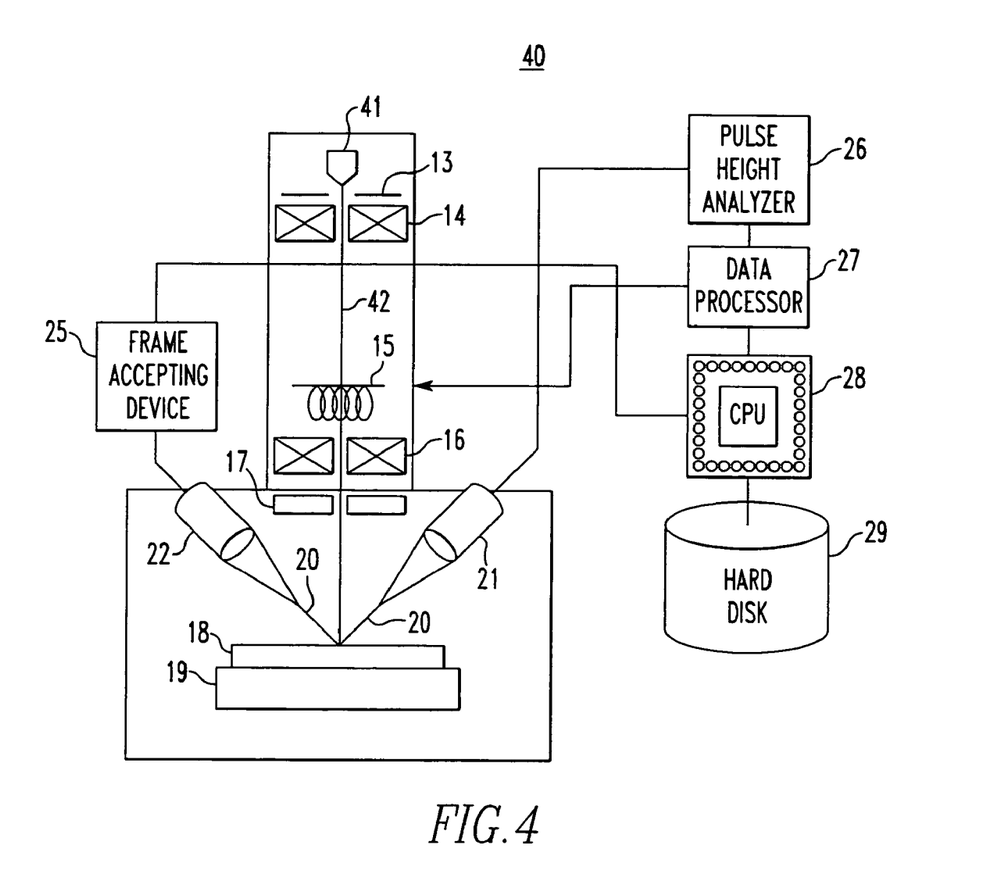
FIG. 4 is a diagram showing the structure of a surface analysis instrument according to another embodiment of the present invention.

FIG. 4 is a diagram of an ion probe microanalyzer according to another embodiment of the present invention.

The ion probe microanalyzer, generally indicated by reference numeral 40, uses a focused ion beam source 41 to direct an ion beam 42 at a sample instead of the electron beam source 11 of the above-described electron probe microanalyzer 10. This surface analysis instrument 40 is similar in structure and operation with the electron probe microanalyzer 10 (FIG. 1) except that the focused ion beam source 41 is used to produce the ion beam 42. Those components which are identical in both FIGS. 1 and 4 are indicated by the identical numerals in FIGS. 1 and 4 and their description is omitted. The ion probe microanalyzer 40 can reproduce spectra using a data structure similar to the data structure used by the surface analysis instrument 10.

It is to be understood that the embodiments described so far are merely some embodiments of the present invention and that the invention is not limited thereto.

Having thus described my invention with the detail and particularity required by the Patent Laws, what is desired protected by Letters Patent is set forth in the following claims.

The invention claimed is:

1. A method of obtaining and processing data obtained by measurements using a surface analysis instrument, said method comprising the steps of:
    exciting a sample to produce secondary rays;
    detecting the secondary rays;
    analyzing energies of the detected secondary rays;
    creating energy data blocks including (i) tags indicative of being data about the analyzed energies and (ii) data about the energies and creating elapsed time data blocks including (i) tags indicative of being data about elapsed times of measurement and (ii) data about the elapsed times; and
    recording said created energy data blocks and said created elapsed time data blocks in a storage medium.

2. A method as set forth in claim 1, wherein in said step of creating the energy data blocks and the elapsed time data blocks, effective elapsed time data blocks each including (i) a tag indicative of being data about an effective elapsed time and (ii) data about the effective time are also created.

3. A method as set forth in claim 1, wherein in said step of creating the energy data blocks and the elapsed time data blocks, the energy data blocks and the elapsed time data blocks are created whenever secondary rays are entered.

4. A method as set forth in claim 1, wherein during said step of recording said created energy data blocks and said created elapsed time data blocks in a storage medium, said energy data blocks whose number is variable are placed between adjacent ones of said elapsed time data blocks according to the secondary rays.

5. A data structure of data obtained by measurements using a surface analysis instrument, said data structure comprising:
    a variable number of energy data blocks arranged between adjacent ones of elapsed time data blocks according to detected secondary rays produced by exciting a sample;
    wherein the energy data blocks include (i) tags indicative of being data about analyzed energies of the detected secondary rays and (ii) data about the energies; and
    wherein the elapsed time data blocks include (i) tags indicative of being data about elapsed times of measurement and (ii) data about the elapsed times.

6. A method of reproducing a spectrum from data obtained by measurements of secondary rays using a surface analysis instrument, said method comprising the steps of:
    exciting a sample to produce the secondary rays;
    detecting the produced secondary rays;
    analyzing energies of the detected secondary rays;
    creating energy data blocks including (i) tags indicative of being data about the analyzed energies and (ii) data about the energies and creating elapsed time data blocks including (i) tags indicative of being data about elapsed times of measurement and (ii) data about the elapsed times;
    recording said created energy data blocks and said created elapsed time data blocks in a storage medium; and reproducing the energy data blocks according to the elapsed time data blocks recorded in the storage medium and displaying the energy data blocks.

7. A method as set forth in claim 6, wherein in said step of creating the energy data blocks and the elapsed time data blocks, the energy data blocks and the elapsed time data blocks are created whenever secondary rays are entered.

8. A method as set forth in claim 6, wherein in said step of recording said created energy data blocks and said created elapsed time data blocks in a storage medium, said energy data blocks whose number is variable are placed between adjacent ones of said elapsed time data blocks according to the secondary rays.

9. A method of obtaining and processing data obtained by measurements using a surface analysis instrument, said method comprising the steps of:
   exciting a sample to produce secondary rays;
   detecting the produced secondary rays;
   analyzing energies of the detected secondary rays;
   creating energy data blocks including (i) tags indicative of being data about the analyzed energies and (ii) data about the energies such that data about elapsed times of measurement are contained in said energy data blocks; and
   recording said created energy data blocks in a storage medium.

10. A method as set forth in claim 9, wherein during said step of recording said created energy data blocks and said created elapsed time data blocks in a storage medium, information about two-dimensional positions is also stored in said energy data blocks.

11. A data structure of data obtained by measurements using a surface analysis insturument, said data structure comprising:
   an arrangement of energy data blocks which include (i) tags indicative of being data about analyzed energies of detected secondary rays produced by exciting a sample, (ii) data about the energies, and (iii) data about elapsed times of measurement.

12. The data structure of claim 11, wherein information about two-dimensional positions is also stored in said energy data blocks.

13. A method of obtaining and processing data obtained by measurements using a surface analysis instrument, said method comprising the steps of:
   exciting a sample to produce secondary rays;
   detecting the produced secondary rays;
   analyzing energies of the detected secondary rays;
   creating energy data blocks including (i) tags indicative of being data about the analyzed energies, (ii) data about the energies, and (iii) data about elapsed times of measurement;
   controlling the created energy data blocks and recording these energy data blocks in a storage medium; and
   reproducing and displaying the recorded energy data blocks along said elapsed times.

14. A method as set forth in claim 13, wherein during said step of recording said created energy data blocks in a storage medium, information about two-dimensional positions is also stored in said energy data blocks.

15. A surface analysis instrument for analyzing a surface of a sample, said surface analysis instrument comprising:
   a beam source for producing a particle beam directed at the sample;
   detection means for detecting secondary rays produced by exciting the sample with the particle beam supplied from said beam source;
   analysis means for analyzing energies of the secondary rays detected by said detection means;
   data processing means for creating energy data blocks and elapsed time data blocks, the energy data blocks including (i) tags indicative of being data about the analyzed energies and (ii) data about the energies, the elapsed time data blocks including (i) tags indicative of being data about elapsed times of measurement and (ii) data about the elapsed times; and
   control means for recording the energy data blocks and the elapsed time data blocks created by said data processing means into a storage medium.

* * * * *